United States Patent [19]

Ichikawa et al.

[11] Patent Number: 4,547,191
[45] Date of Patent: Oct. 15, 1985

[54] MEDICAL SOLUTION TRANSFUSION CIRCUIT

[75] Inventors: Toshiji Ichikawa, Tokyo; Yoshinori Ohhachi, Kawasaki; Zensho Kanda, Yamanashi, all of Japan

[73] Assignee: Terumo Kabushiki Kaisha, Tokyo, Japan

[21] Appl. No.: 640,386

[22] Filed: Aug. 13, 1984

[30] Foreign Application Priority Data

Aug. 24, 1983 [JP] Japan .................................. 58-153072

[51] Int. Cl.$^4$ ............................................. A61M 5/16
[52] U.S. Cl. ............................................................ 604/251
[58] Field of Search ............................................ 604/251

[56] References Cited

U.S. PATENT DOCUMENTS 4,117,035  9/1978  Hillier et al. ...................... 604/251
4,170,994  10/1979  Komatsu ............................ 604/251

FOREIGN PATENT DOCUMENTS 1153657  3/1980  Canada ............................... 604/251

Primary Examiner—R. L. Andrews
Attorney, Agent, or Firm—Frishauf, Holtz, Goodman & Woodward

[57] ABSTRACT

A medical solution transfusion circuit has a transparent cylindrical pumping body, a hard cap mounted on at least one end of said transparent cylindrical pumping body, and a flexible tube for communicating with said transparent cylindrical pumping body to transport a medical solution. The transparent cylindrical pumping body comprises a propylene/α-olefin copolymer.

14 Claims, 3 Drawing Figures

FIG. 2
FIG. 3
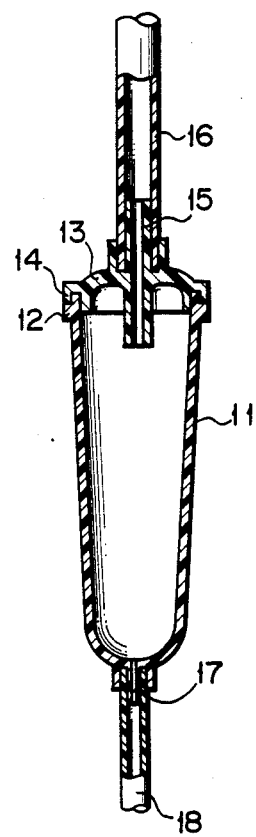
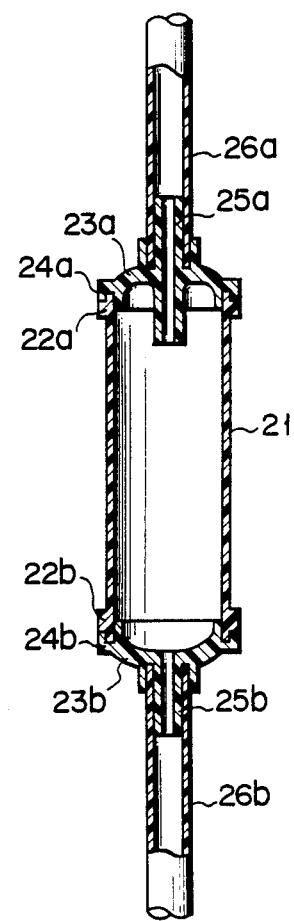

MEDICAL SOLUTION TRANSFUSION CIRCUIT

BACKGROUND OF THE INVENTION (1) Field of the Invention

The present invention relates to a medical solution transfusion circuit having a cylindrical pumping body such as a drip chamber in a solution administration or blood administration set and, more particularly, to a medical solution transfusion circuit which can be easily assembled by ultrasonic welding and which has a cylindrical body suitable for radiation sterilization and having good pumping characteristics and high transparency.

(2) Description of the Prior Art

Conventional circuits are used to transfuse medical solutions such as an infusion solution and blood in medical treatments (e.g., solution administration or blood administration) and extracorporeal blood circulation treatments (e.g., dialysis and artifical heart and lung treatment). These medical solution transfusion circuits each comprise a cylindrical body such as a drip chamber having a drip port for dripping a medical solution in the drip chamber, and a flexible tube connected to the drip chamber to transport the medical solution. In this case, the drip chamber is transparent to allow checking of a drip rate of the medical solution.

Flexible tubes for transfusing a medical solution are connected to two ends of the cylindrical body which is made of flexible or semi-rigid vinyl chloride resin and incorporated in the medical solution transfusion circuit. When the medical solution transfusion circuit is assembled, the two ends of the cylindrical body are adhered by an organic solvent such as cyclohexanone and tetrahydrofuran to the separately formed components such as drip port members and the flexible tubes. Alternatively, the two ends of the cylindrical body are adhered by an organic solvent to a hard cap having the drip port formed therein.

However, when an organic solvent is used as an adhesive, the solvent permeates into the inner space or inside the material at the adhered portion and its vicinity and is left there. The solvent left inside the material weakens the mechanical strength of the material. In addition to this disadvantage, the solvent left in the inner space may be eluted in the medical solution when the cylindrical body is used. These disadvantages cause grave problems in the medical solution transfusion circuit.

In addition, the flexible vinyl chloride resin has a low elasticity and cannot restore its original shape when pumping occurs. However, even when the amount of a plasticizer is decreased to improve the restoration force, crazing occurs if the cylindrical body pumps several times. Furthermore, when the flexible vinyl chloride resin is sterilized with gamma-rays, the resin is discolored, and an amount of extract increases. In addition to these disadvantages, a pH value greatly changes, and consumption of potassium permanganate is increased.

A flexible transparent material subjected to pumping comprises an ethylene-vinyl acetate copolymer, an ethylene-ethylacrylate copolymer, a styrene-butadiene based copolymer, or a denaturated copolymer of poly(4-methylpentene-1). When the denaturated copolymer is formed into a thin cylindrical body, it may be crushed and cracked by pumping, and microorganisms may be introduced into the medical solution. This denaturated copolymer is thus not suitable as a material for a drip chamber. The styrene-butadiene copolymer is not practically used since a drip chamber thereof is easily crushed by pumping and will not restore its initial cylindrical shape. The ethylene-ethylacrylate copolymer is toxic due to the presence of ethylacrylate. The ethylene-vinyl acetate copolymer is not sufficiently transparent. The above copolymers absorb ultrasonic vibrations due to their flexibility when they are welded by an ultrasonic welder and thus are not suitable for ultrasonic welding.

SUMMARY OF THE INVENTION

It is an object of the present invention to provide a medical solution transfusion circuit which can be easily assembled by ultrasonic welding and which has a cylindrical body suitable for radiation sterilization and having good pumping characteristics and high transparency.

In order to achieve the above object of the present invention, there is provided a medical solution transfusion circuit having a transparent cylindrical pumping body, a hard cap mounted on at least one end of said transparent cylindrical pumping body, and a flexible tube for communicating with said transparent cylindrical pumping body to transfuse a medical solution, wherein said transparent cylindrical pumping body comprises a propylene/α-olefin copolymer.

The propylene/α-olefin copolymer is a copolymer of propylene and α-olefin and has a weight average molecular weight of 20,000 to 1,000,000 and preferably 50,000 to 500,000. α-olefin as a monomer comprises ethylene, butene-1, pentene-1, 4-methylpentene-1 or a combination thereof. The content of α-olefin is 50 to 2% by weight, preferably 40 to 3% by weight. More preferably, when α-olefin contains 4 or more carbon atoms, the content of α-olefin is 35 to 7% by weight, and the content of ethylene is 20 to 2% by weight. When the content of α-olefin exceeds 50% by weight in the copolymer, the resultant cylindrical pumping body becomes too soft, and is poor in restoring force and in high frequency fusability with polypropylene. However, when the content of α-olefin is less than 2% by weight, the mechanical strength of the resultant cylindrical body is weakened, and cracks may form upon pumping.

An ethylene/α-olefin copolymer may be mixed in the propylene/α-olefin copolymer. The content of the ethylene/α-olefin copolymer is not more than 30% by weight and preferably not more than 15% by weight. When the content of ethylene/α-olefin copolymer exceeds 30% by weight, the flexible cylindrical body becomes excessively soft, thus lowering the restoration force upon pumping and weakening a portion ultrasonically welded with polypropylene.

A nucleating agent may be mixed in the propylene/α-olefin copolymer to further improve the molding characteristics. In addition, bleeding, which frequently occurs in flexible olefin-based resins, can be thereby reduced. The content of the nucleating agent is 0.5 to 0.05% by weight and preferably 0.3 to 0.1% by weight. The nucleating agent is selected from dibenzal sorbitol, tribenzal sorbitol, di(methylbenzal)sorbitol, and tri(methylbenzal)sorbitol. The propylene/α-olefin copolymer constituting the flexible cylindrical body is colorless and transparent. When this copolymer is measured by, e.g., ASTMD1003, a haze level is not more than 20%, preferably not more than 15%, and more preferably not more than 10%. A modulus of elasticity is 10,000 to 1,000 kg/cm$^2$, and preferably 8,000 to 3,000 kg/cm$^2$.

The hard cap preferably comprises polypropylene, especially polypropylene having a weight average molecular weight of 80,000 to 900,000 and preferably 100,000 to 500,000. A filler (including a reinforcing agent) may be mixed in the polypropylene. The filler or reinforcing agent comprises glass fibers, carbon fibers, mica, talc or calcium carbonate. The content of the filler or reinforcing agent is preferably 10% to 50% by weight (with respect to the content of polypropylene). A mixture (see Japanese Patent Disclosure (Kokai) No. 58-165856) of hindered amine, phenol or its phosphorus ester, a nucleating agent or the like may be used to prevent radiation degradation of polypropylene.

The medical solution transfusion circuit according to the present invention can be sterilized in accordance with one of various methods. These include, for example, autoclaving, gas sterilization by ethylene oxide gas, and radiation sterilization. Radiation sterilization is preferable since neither thermal deformation occurs nor a residual gas is left. The radiation may be gamma rays, electron rays or the like. When gamma rays are used, a satisfactory sterilization is obtained with a small dose. In general, the radiation dose is 1 to 5M rad, and preferably 1.5 to 4M rad.

Radiation sterilization has an advantage in that an ultraviolet-curing adhesive can be used in place of ultrasonic welding adhesive to adhere the cylindrical body and the hard cap and cure the adhesive by utilizing the sterilization radiation energy.

BRIEF DESCRIPTION OF THE DRAWINGS

FIGS. 2 and 3 are sectional views of cylindrical pumping bodies in medical solution transfusion circuits according to other embodiments of the present invention.

DETAILED DESCRIPTION OF THE PREFERRED EMBODIMENTS

Figure 1:
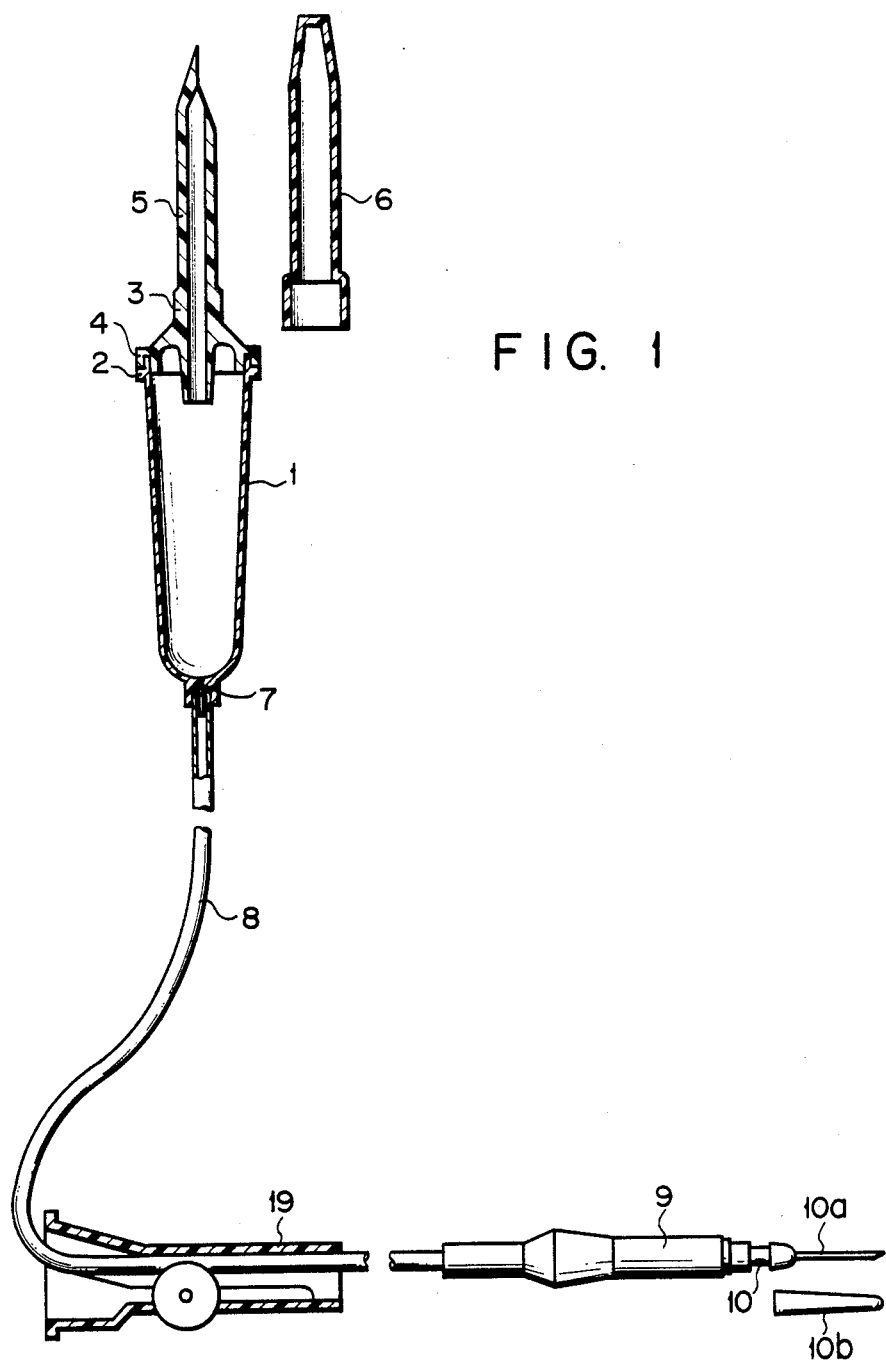
FIG. 1 is a sectional view showing part of a medical solution transfusion circuit according to an embodiment of the present invention.

The present invention will be described in detail with reference to the accompanying drawings. FIG. 1 shows a solution administration set having a drip chamber. A flange 2 formed at the distal end of the opening of a flexible transparent cylindrical body 1 prepared by injection-molding a propylene/α-olefin copolymer is engaged with a flange 4 formed in the vicinity of the distal portion of a hard cap 3 prepared by injection-molding polypropylene or the like. A vibrator (not shown) of an ultrasonic welder is operated from the side of the flange 4 to perform ultrasonic welding, thereby forming a drip chamber. A spike needle 5 is formed integrally with the cap 3 and is covered with a protection cap 6 as needed. A port 7 is formed at the other end of the cylindrical body 1. A flexible tube 8 is connected to the port 7 to transfuse a medical solution. A soft rubber connector 9 (if needed) and a hard connector 10 are connected to the distal end of the flexible tube 8. A phlebotomy needle 10a for insertion into a vein is coupled to the distal end of the connector 10. The phlebotomy needle 10a is covered with a protection cap 10b as needed. A clamp 19 is mounted midway along the flexible tube 8 so as to clamp it.

The medical solution transfusion circuit having the above construction is used in the following manner.

The protection cap 6 is removed from the spike needle 5, and the spike needle 5 is inserted into an infusion solution bag through a rubber stopper (not shown) serving as a mixing port. The cylindrical body 1 of the drip chamber is pressed once or several times to discharge bubbles from the tube to the infusion solution bag, and the medical solution flows in the drip chamber. When the medical solution is stored in part (e.g., ½) of the space of the drip chamber, the solution starts to flow in the tube 8. When the solution starts to drip from the phlebotomy needle, the bubbles inside the tubes are completely removed. The phlebotomy needle is inserted into a vein of a patient, and the clamp 19 is adjusted to control the drip rate of the medical solution.

FIG. 2 shows another embodiment of the present invention. A flange 12 formed at the distal end of the opening of a flexible transparent cylindrical body 11 prepared by injection-molding a propylene/α-olefin copolymer is engaged with a flange 14 formed in the vicinity of the distal portion of a hard cap 13 prepared by injection-molding polypropylene or the like. A vibrator (not shown) of an ultrasonic welder is operated from the side of the flange 14 to perform ultrasonic welding, thereby forming a drip chamber. A port 15 is formed in the cap 13. A flexible tube 16 is connected to the port 15 to transfuse the medical solution. A port 17 is formed at one end of the cylindrical body 11 and is connected to a flexible tube 18 to transfuse the medical solution. A connector (not shown) is coupled to the distal end of the flexible tube 18 as needed, as in FIG. 1. A clamp (not shown) is mounted midway along the tube 18 as needed so as to clamp it.

FIG. 3 shows still another embodiment of the present invention. Flanges 22a and 22b formed in the vicinity of the distal ends of two ends of a flexible transparent cylindrical body 21 prepared by injection-molding a propylene/α-olefin copolymer are engaged with flanges 24a and 24b formed in the vicinity of the distal end openings of hard caps 23a and 23b prepared by injection-molding polypropylene or the like, respectively. Vibrators (not shown) of an ultrasonic welder are operated to perform untrasonic welding from the sides of the flanges 24a and 24b, respectively, thereby preparing a drip chamber. Ports 25a and 25b are formed in the caps 23a and 23b, respectively. Flexible tubes 26a and 26b are respectively coupled to the ports 25a and 25b to transfuse the medical solution. A needle is connected to the distal end of the tube 26a, and a connector and a canula are connected to the distal end of the tube 26b in the same manner as in FIG. 1.

The present invention has been described mainly by exemplifying a solution administration set. However, the present invention is not limited to this application, but may be extended to include a medical solution transfusion circuit having a cylindrical pumping body. For example, the present invention can be applied to a blood administration set, and an extracorporeal circulation circuit used for artificial lungs and an artificial heart.

The present invention will be described in detail by way of examples.

EXAMPLE 1

A hard cap having a spike needle 5, as shown in FIG. 1, was prepared by injection-molding polypropylene containing 0% to 3% by weight of ethylene and having a weight average molecular weight of about 250,000. A flexible transparent cylindrical body 1 having a port 7 at its one end, as shown in FIG. 1, was prepared by injection-molding a propylene/α-olefin copolymer (α-olefin:1-buten) (tradename: "TOUGHMER XR-106"

available from Mitsui Petrochemical Industries, Ltd. Tokyo, Japan) having a weight average molecular weight of about 300,000. A flange 2 of the cylindrical body 1 was engaged with a flange 4 of the cap 3 and was welded by ultrasonic welding to prepare a drip chamber. A flexible vinyl chloride tube 8 was coupled to the port 7 of the obtained drip chamber, and connectors 9 and 10 and a phlebotomy needle 10a were coupled to the distal end of the tube 8.

The thus obtained solution administration set was sterilized with gamma-rays of 3 Mrad. An extraction test and a biological test of the sterilized solution administration set was conducted in accordance with Notification No. 301 "Standards of Disposable Blood Administration and Solution Administration Set" of the Ministry of Health and Welfare on Aug. 10, 1970, and the results shown in Table 1 were obtained. Other test results (haze level and hue) on the flexible transparent cylindrical body were also obtained, as shown in Table 1. The haze level (transmittance) was measured by a ASTMD1003.

EXAMPLE 2

A hard cap 13, as shown in FIG. 2, was prepared by injection-molding a polypropylene compound obtained by mixing 5% to 40% by weight of glass fiber with polypropylene containing 0 to 3% by weight of ethylene and having a weight average molecular weight of about 200,000. A flexible transparent cylndrical body 11 having a port 17 at its one end, as shown in FIG. 2, was prepared by injection-molding a propylene/α-olefin copolymer (α-olefin:ethylene) (tradename: "SPX-8400" available from Mitsubishi Petrochemical Co., Ltd. Tokyo, Japan) having a weight average molecular weight of about 200,000. A flange 12 of the cylindrical body 11 and a flange 14 of the cap 13 were welded by ultrasonic welding, and the resultant apparatus was sterilized with gamma-rays in the same manner as in Example 1. The sterilized set was then tested, and the test results were obtained, as shown in Table 1.

COMPARATIVE EXAMPLE

A hard cap 3 was prepared by injection-molding a hard vinyl chloride resin (average polymerization degree of 800). A flexible vinyl chloride resin (having an average polymerization degree of 1100 and containing 40% by weight of di-2-hetylhexyl phthalate) was blow-formed to prepare a flexible transparent cylindrical body 1. The hard cap 3 was adhered by a cyclohexanone solvent to the cylindrical body 1 to prepare a drip chamber. All other processes were the same as those of Example 1. The resultant dip chamber was sterilized with gamma-rays, and the test results were obtained, as shown in Table 1.

TABLE 1

| Item (Reference value) | Example 1 | Example 2 | Comparative Example |
|---|---|---|---|
| ΔpH (2.0 or less) | 1.2 | 0.8 | 2.8 |
| Heavy metal (2.0 ml or less) | 2.0 ml or less | 2.0 ml or less | 2.0 ml or less |
| ΔK MnO4 (2.0 ml or less) | 0.7 | 0.5 | 1.2 |
| Evaporated residue (1.0 ml or less) | 0.0 | 0.0 | 0.3 |
| Pyrogenicity test | good | good | good |
| Acute toxicity test | good | good | good |
| Skin test | good | good | good |
| Haze (%) | 7 | 6 | — |
| Hue | colorless | colorless | dark brown; |

TABLE 1-continued

| Item (Reference value) | Example 1 | Example 2 | Comparative Example |
|---|---|---|---|
| | transparent | transparent | transparent |

According to the present invention, in a medical solution transfusion circuit including a cylindrical member having a hard cap and a flexible transparent cylindrical body and further including a flexible tube coupled to the cylindrical body so as to transport the medical solution, the flexible cylindrical body is made of a propylene/α-olefin copolymer, the flexible cylindrical body is adhered to the hard cap, and the resultant drip chamber is sterilized. The drip chamber has good resistance to radiation sterilization, good pumping characteristics and is free from crazing.

When the hard cap is made of polypropylene, the cap can be properly welded with the copolymer by ultrasonic welding. When the content of α-olefin in the propylene/α-olefin copolymer is 50 to 2% by weight, and the α-olefin comprises butene-1, the cylindrical body has excellent resistance to radiation sterilization. The cylindrical body and the associated components are molded by injection molding. Ultrasonic welding can thus be simply performed to improve the mechanical strength of the welded portions. When the cylindrical body constitutes a drip chamber, especially good effects can be obtained from the viewpoint of sanitary safety. In addition, when the flexible cylindrical body is welded with the hard cap by ultrasonic welding, the bonding strength therebetween is high. In this case, sterilization may be performed by using gamma-rays, and so no sterilizer is left in the apparatus.

What is claimed is:

1. A medical solution transfusion circuit having a transparent cylindrical pumping body, a hard cap mounted on at least one end of said transparent cylindrical pumping body, and a flexible tube for communicating with said transparent cylindrical pumping body to transport a medical solution, wherein said transparent cylindrical pumping body comprises a propylene/α-olefin copolymer.

2. A circuit according to claim 1, wherein said hard cap comprises polypropylene or polypropylene containing a filler.

3. A circuit according to claim 2, wherein polypropylene has a weight average molecular weight of 80,000 to 900,000.

4. A circuit according to claim 2, wherein said filler is a material selected from the group consisting of a glass fiber, a carbon fiber, mica, talc and calcium carbonate.

5. A circuit according to claim 1, wherein a content of α-olefin in the propylene/α-olefin copolymer falls within a range between 50% by weight and 2% by weight.

6. A circuit according to claim 3, wherein the α-olefin comprises butene-1.

7. A circuit according to claim 1, wherein the α-olefin comprises a combination of ethylene and butene-1.

8. A circuit according to claim 1, wherein the α-olefin is a material selected from the group consisting of ethylene, butene-1, pentene-1 and 4-methylpentene-1.

9. A circuit according to claim 1, wherein said cylindrical body is made of a propylene/α-olefin copolymer and not more than 30% by weight of an ethylene/α-olefin copolymer.

10. A circuit according to claim 1, wherein the propylene/α-olefin copolymer has a weight average molecular weight falling within a range between 20,000 and 1,000,000.

11. A circuit according to claim 1, wherein the propylene/α-olefin copolymer contains 0.5 to 0.05% by weight of a nucleating agent.

12. A circuit according to claim 1, wherein the propylene/α-olefin copolymer has a modulus of elasticity of 10,000 to 1,000 kg/cm$^2$.

13. A circuit according to claim 1, wherein said cylindrical body constitutes a drip chamber.

14. A circuit according to claim 1, wherein said flexible cylindrical body and said hard cap are directly adhered by fusion.

* * * * *